(12) United States Patent
Chin

(10) Patent No.: US 11,351,003 B2
(45) Date of Patent: Jun. 7, 2022

(54) APPARATUS AND METHOD FOR ORAL AND MAXILLOFACIAL SURGERY AND PREOPERATIVE MODELING

(71) Applicant: Martin Chin, Corte Madera, CA (US)

(72) Inventor: Martin Chin, Corte Madera, CA (US)

( * ) Notice: Subject to any disclaimer, the term of this patent is extended or adjusted under 35 U.S.C. 154(b) by 1496 days.

(21) Appl. No.: 15/200,443

(22) Filed: Jul. 1, 2016

(65) Prior Publication Data
US 2016/0310227 A1 Oct. 27, 2016

Related U.S. Application Data

(62) Division of application No. 13/662,068, filed on Oct. 26, 2012, now Pat. No. 9,381,315.

(51) Int. Cl.
*A61B 90/14* (2016.01)
*A61C 11/02* (2006.01)
(Continued)

(52) U.S. Cl.
CPC ............ *A61B 90/14* (2016.02); *A61B 17/176* (2013.01); *A61C 11/00* (2013.01); *A61C 11/02* (2013.01); *A61C 11/08* (2013.01); *A61C 19/04* (2013.01); *A61M 16/01* (2013.01); *A61M 16/0461* (2013.01); *A61M 16/0497* (2013.01); *A61M 16/0875* (2013.01); *A61C 13/34* (2013.01);
(Continued)

(58) Field of Classification Search
CPC ....... A61B 90/14; A61B 17/176; A61C 11/02; A61C 11/08; A61C 19/04
See application file for complete search history.

(56) References Cited

U.S. PATENT DOCUMENTS 2,702,550 A 2/1955 Rowe
2,951,482 A 9/1960 Sullivan
(Continued)

OTHER PUBLICATIONS

Walter Lorenz Surgical Instruments, Instruction Manual, O.S.S.I. "J", 1984, 16 pages.
(Continued)

*Primary Examiner* — Kevin T Truong
*Assistant Examiner* — Tracy L Kamikawa
(74) *Attorney, Agent, or Firm* — Vierra Magen Marcus LLP

(57) ABSTRACT

A head frame apparatus is secured to a human head during maxillofacial surgery and includes devices to easily position and secure an endotracheal (breathing) tube and an anesthesia delivery circuit for the patient that reduces the likelihood that the flow of oxygen through the tube is restricted thereby reducing the risk of severe injury or death. The head frame apparatus also includes a removable reference indicator, which may be easily attached and removed while identifying a reference point of the patient's face. Also the reference indicator includes a universal joint and pointer with an attached ruler. A transport apparatus positions multiple preset reference indicators and allows for preoperative transportation and removal, while protecting the preset reference indicators from inadvertent adjustment. A bendable reference indicator used in an articulator for preoperative modeling allows for easily identifying reference points in a cast model. An orbiting segment apparatus positions a portion of a cast of a jaw in relation to a condyle ball of the articulator.

8 Claims, 14 Drawing Sheets

(51) Int. Cl.
  *A61C 11/08* (2006.01)
  *A61C 19/04* (2006.01)
  *A61C 11/00* (2006.01)
  *A61M 16/01* (2006.01)
  *A61M 16/04* (2006.01)
  *A61B 17/17* (2006.01)
  *A61M 16/08* (2006.01)
  *A61C 13/34* (2006.01)

(52) U.S. Cl.
  CPC ... *A61M 16/0833* (2014.02); *A61M 2209/088* (2013.01); *A61M 2210/06* (2013.01)

(56) References Cited

U.S. PATENT DOCUMENTS

| | | | |
|---|---|---|---|
| 2,966,383 | A | 12/1960 | Boetcker et al. |
| 3,099,441 | A | 7/1963 | Ries |
| 3,835,861 | A | 9/1974 | Kees, Jr. et al. |
| 4,108,426 | A | 8/1978 | Lindstroem et al. |
| 4,163,319 | A | 8/1979 | Ouaknine |
| 4,358,269 | A * | 11/1982 | Hay .................. A61C 11/08 433/60 |
| 4,391,589 | A | 7/1983 | Monfredo et al. |
| 4,392,645 | A | 7/1983 | Westphal |
| 4,465,069 | A | 8/1984 | Barbier et al. |
| 4,475,550 | A | 10/1984 | Bremer et al. |
| 4,573,917 | A | 3/1986 | Erickson |
| 4,612,928 | A | 9/1986 | Tiep et al. |
| 4,612,929 | A | 9/1986 | Schubert et al. |
| 4,612,930 | A | 9/1986 | Bremer |
| 4,638,798 | A | 1/1987 | Shelden et al. |
| 4,667,660 | A | 5/1987 | Eingom |
| 4,706,665 | A | 11/1987 | Gouda |
| 4,744,358 | A | 5/1988 | McGinnis |
| 4,774,946 | A | 10/1988 | Ackerman et al. |
| 5,402,776 | A | 4/1995 | Islava |
| 6,726,479 | B2 | 4/2004 | Tremont |
| 7,730,563 | B1 * | 6/2010 | Sklar .................. A61G 13/121 5/637 |
| 2003/0138755 | A1 | 7/2003 | Tremont |
| 2007/0055289 | A1 * | 3/2007 | Scouten .................. A61B 90/14 606/130 |
| 2007/0079832 | A1 | 4/2007 | Baldauf |
| 2011/0240034 | A1 | 10/2011 | Ciccone |
| 2012/0295219 | A1 * | 11/2012 | Monteiro Geras .... A61C 11/08 433/55 |

OTHER PUBLICATIONS

Ellis et al., Use of the Orthognathic Surgery Simulating Instrument in the Presurgical Evaluation of Facial Asymmetry, J. Oral Maxillofac Surg, Case Reports, 1984, pp. 805-811.

Heggie, A.A.C., "A calibrator for monitoring maxillary incisor position during orthognathic surgery," Department of Oral and Maxillofacial Surgery, Royal Melbourne Hospital, Dec. 1987, pp. 671-673.

Johnson, D.G., "Intraoperative measurement of maxillary repositioning: An ancillary technique," McMaster University, Sep. 1985, pp. 266-268.

McChance, A.M. et al., "Le Fort I maxillary osteotomy: is it possible to accurately produce planned pre-operative movements?," British Journal of Oral and Maxillofacial Surgery, Jun. 1992, pp. 369-376.

Schudy, George F., "Incisal Locator for Orthognathic Surgery," JPO Inc., Oct. 1981, pp. 672-675.

Speculand, Bernard, et al., "A Halo-Caliper Guidance System for Bi-Maxillary (Dual-Arch) Orthognathic Surgery," J. max.-fac. Surg. 12, 1984, Oct. 11, 1983, pp. 167-173.

Response to Election/Restriction dated Nov. 25, 2014 in U.S. Appl. No. 13/662,068.

Requirement for Restriction/Election dated Sep. 25, 2014 in U.S. Appl. No. 13/662,068.

Notice of Allowance and Fees Due dated Mar. 2, 2016 in U.S. Appl. No. 13/662,068.

Non-Final Rejection dated Aug. 19, 2015 in U.S. Appl. No. 13/662,068.

Amendment dated Feb. 19, 2016 in U.S. Appl. No. 13/662,068.

* cited by examiner

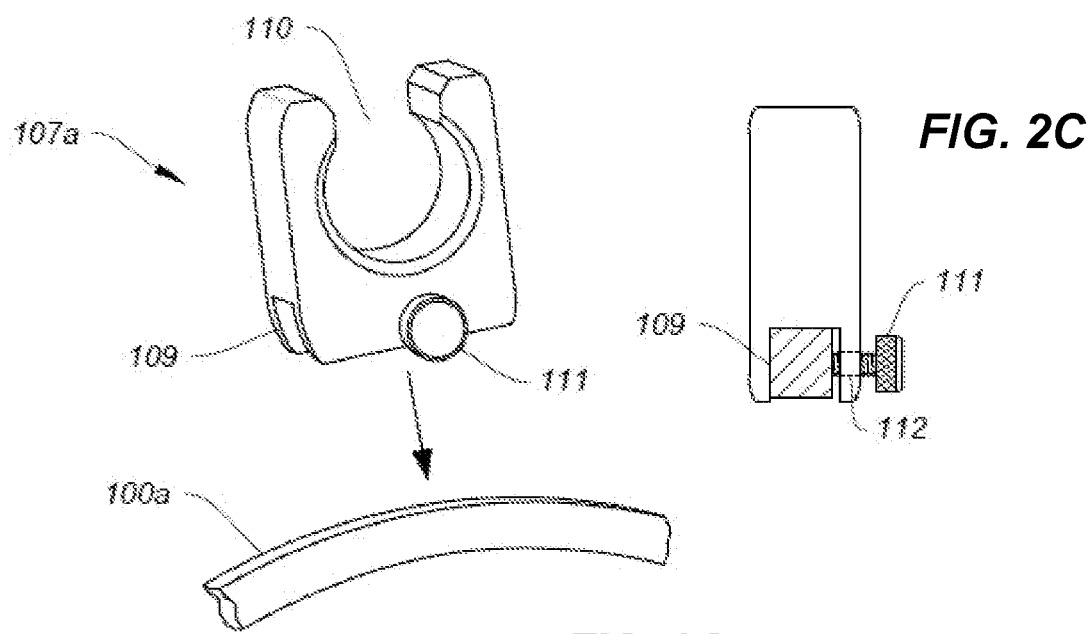
FIG. 2A
FIG. 2C
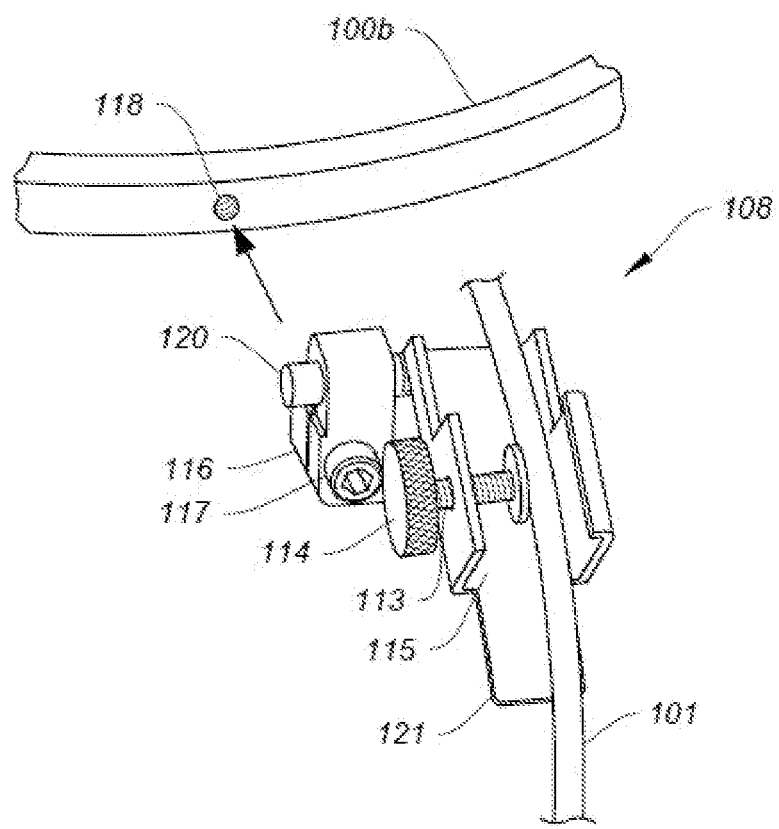
FIG. 2B

FIG. 6D
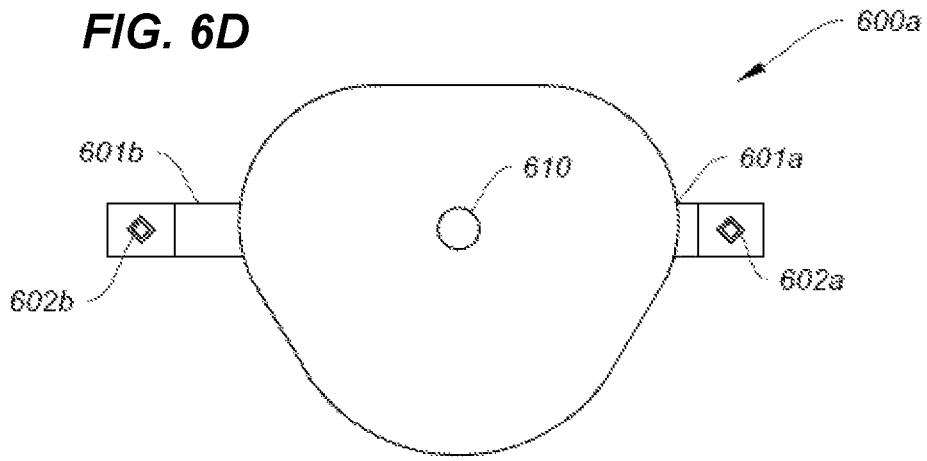
FIG. 6A
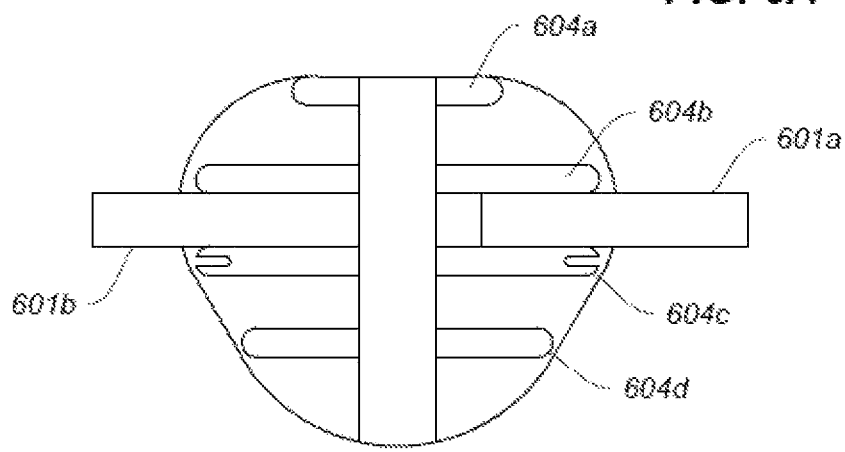
FIG. 6B FIG. 6C
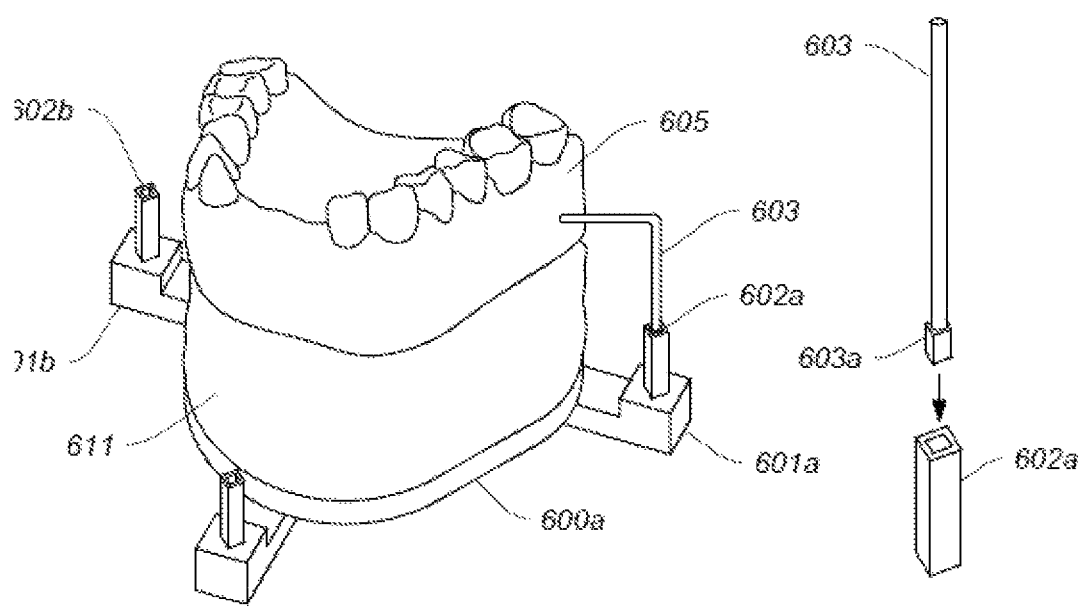

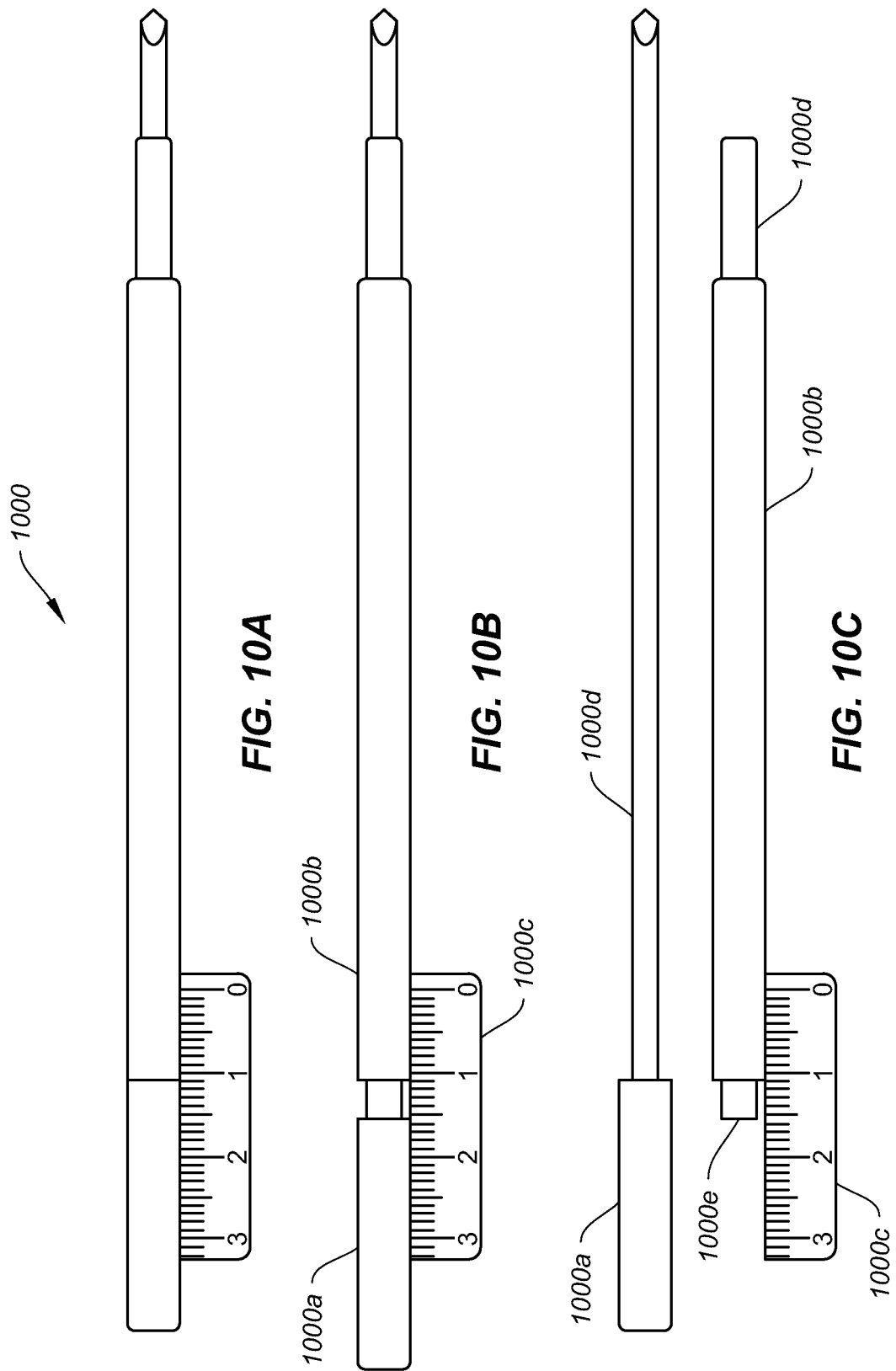

APPARATUS AND METHOD FOR ORAL AND MAXILLOFACIAL SURGERY AND PREOPERATIVE MODELING

PRIORITY CLAIM

This application is a divisional of U.S. patent application Ser. No. 13/662,068 filed Oct. 26, 2012, to be issued as a U.S. Pat. No. 9,381,315.

BACKGROUND

1. Field

The present technology relates to a method and apparatus for oral and maxillofacial surgery and preoperative modeling.

2. Description of Related Art

Oral and Maxillofacial surgery refers to surgery to correct jaw and/or facial abnormalities that may be caused by disease, injuries, abnormal growth, skeletal disharmonies and/or defects in the head, neck, face, jaw and the hard and soft tissues of the oral (mouth) and maxillofacial (jaws and face) region. Oral and Maxillofacial surgery may also be referred to as orthognathic surgery, reconstructive jaw surgery or surgery orthodontics. During maxillofacial surgery it is often critical that the patient be provided with an unrestricted flow of oxygen and anesthetic gases. Typically, an anesthesia endotracheal tube from an anesthesia delivery circuit is taped to the face and inserted into the patient's nose during surgery. However, the endotracheal or breathing tube may be displaced as portions of the patient's face is moved or if there is traction on the anesthesia circuit tubing. If the endotracheal or breathing tube as well as anesthesia delivery circuit is restricted to such an extent that the patient does not receive enough oxygen, the patient may undergo cardiac arrest, which may lead to permanent damage and even death. Therefore, it is desirable to provide a surgical apparatus that increases the likelihood of an unrestricted flow of oxygen during maxillofacial surgery thereby reducing the likelihood of injury to the patient.

Providing accurate reference points, or where certain portions of the face are located or should be located, before beginning and during surgery is extremely important in order to have successful surgical results. For example, if the maxilla (upper jaw) is to be positioned three inches outward from its original position, a fixed reference point where the maxilla is in relationship to the immobilized facial skeleton or cranium is needed before incisions and displacement during surgery occurs.

While it is important to have a device that provides accurate reference points of portions of the face, it is also desirable that the reference points may be easily positioned based on preoperative modeling, adjusted during surgery and removed when they are no longer needed. If the reference points are easily positioned, adjusted and removed, the surgery may take less time and the surgeon may focus on other more critical aspects of the surgery. If the reference points are easily positioned, more accurate surgical results may be likely.

Further, it is desirable that a device that provides a reference point based on preoperative modeling be protected from being inadvertently adjusted before or while the device is used in surgery. A device that provides a reference point could be inadvertently adjusted by a surgical nurse during transportation. The inadvertently adjusted reference point may lead to misaligned surgical results or cause an unnecessary delay during surgery.

Typically before beginning maxillofacial surgery, an articulator is used in preoperative modeling. In particular, an articulator which fixes casts of the maxillary (upper) and mandibular (lower) teeth is used. The articulator with the fixed casts adjusts the position of the mandible in relation to the maxilla. The articulator and the fixed casts allow the surgeon to model a surgery. For example, the surgeon can model where bone cuts and displacement of bones may be made by cutting and repositioning portions of the casts. However, using the articulator to identify fixed reference points of the model or cast may result in the loss of those fixed reference points when the cast is removed from the articulator; thus not allowing further study or modeling.

DESCRIPTION OF THE DRAWINGS

FIGS. 2A and 2C illustrate perspective and edge views of devices coupled to the head frame apparatus to position an anesthesia delivery circuit used in maxillofacial surgery according to an embodiment.

FIG. 2B illustrates a device coupled to the head frame apparatus to position an endotracheal tube used in maxillofacial surgery according to an embodiment.

FIGS. 6A-D illustrate a system to identify reference points of a cast in an articulator used in preoperative modeling according to an embodiment.

FIGS. 10A-C illustrate a reference pointer that may be used in the removable reference indicator shown in FIG. 4 according to an embodiment.

Figure 1:
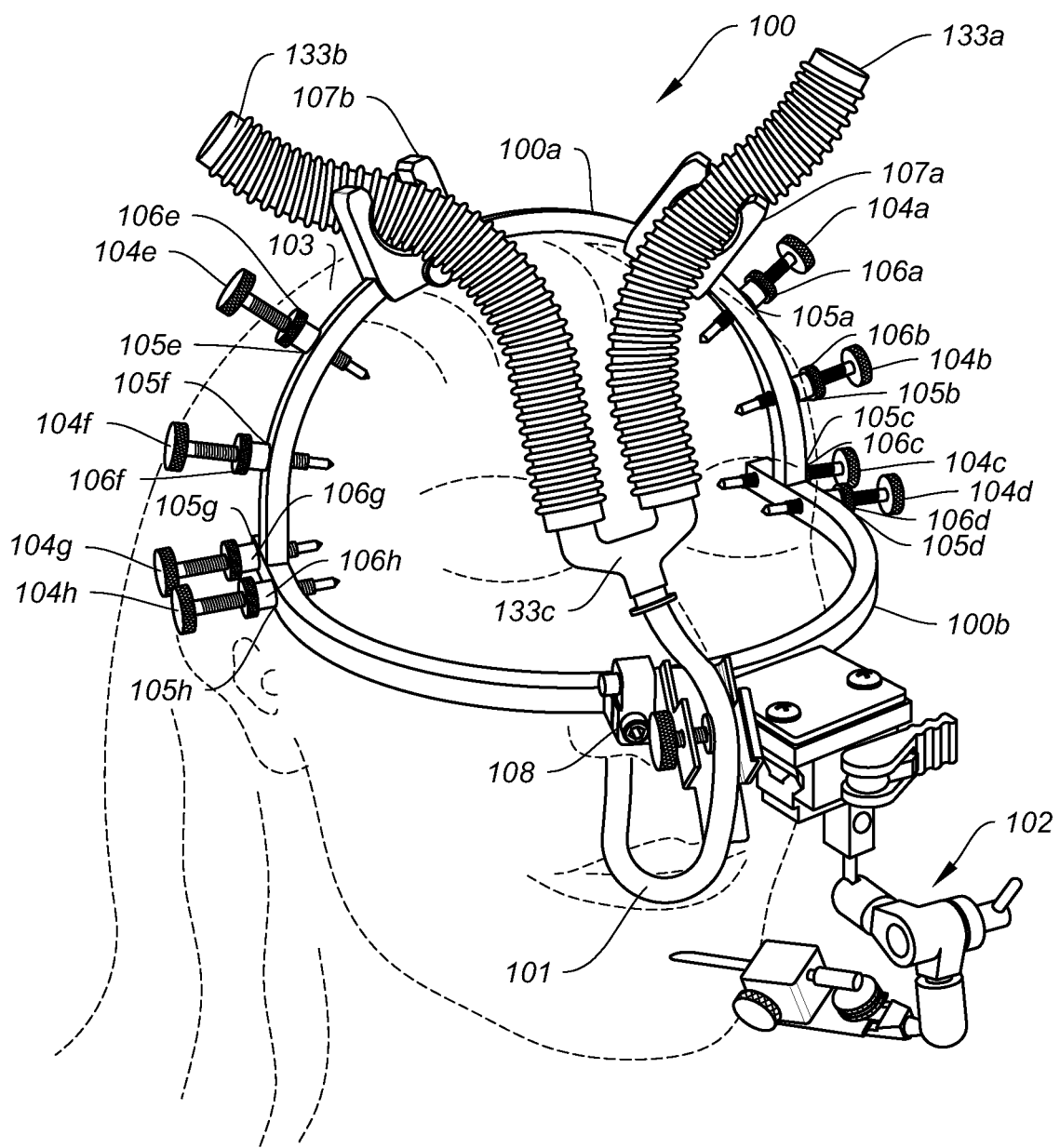
FIG. 1 illustrates a head frame apparatus to position an endotracheal tube and an anesthesia delivery circuit as well as a removable reference indicator used in maxillofacial surgery according to an embodiment.

In the drawing, in which like reference numerals indicate similar elements, and in the following description, numerous specific details are set forth as examples in order to provide a thorough understanding of embodiments. It will be obvious, however, to one skilled in the art, that embodiments may be practiced without some or all of these specific details. In other instances, well known process steps or elements have not been described in detail in order not to unnecessarily obscure a particular embodiment.

DETAILED DESCRIPTION

A head frame apparatus is secured to a human head during maxillofacial surgery and includes devices to easily position and secure an endotracheal (breathing) tube and an anesthesia delivery circuit for the patient that reduces the likelihood that the flow of oxygen through the delivery circuit and tube is restricted thereby reducing the risk of severe injury or death. The head frame apparatus also includes a removable reference indicator, which may be easily attached and removed while identifying a reference point of the patient's face. Also the removable reference indicator includes a universal joint and pointer with an attached ruler. The ease of attaching, removing and using the removable reference indicator typically reduces the amount of time required for surgery and allows for the surgeon to focus on other critical tasks during surgery. A transport apparatus positions multiple preset removable reference indicators and allows for preoperative and operative transportation and removal, while protecting the preset removable reference indicators from inadvertent adjustment. A bendable reference indicator used in an articulator for preoperative modeling allows for easily identifying reference points in a cast model. An orbiting segment apparatus also positions a portion of a cast of a jaw in relation to a condyle ball of the articulator.

The head frame apparatus includes a first arched member to be positioned on top of the human head and a second arched member formed at approximately 90 degrees from the first arched member. A removable rectangular device is coupled to the second arched member to position the endotracheal tube, while two other removable devices are coupled to the first arched member to position the anesthesia delivery circuit. The head frame apparatus also includes a plate coupled to the second arched member having a mount to position the removable reference indicator that identifies a reference point of the human head before and/or during surgery. The head frame apparatus and devices are constructed to minimize the number of pieces that may be used during surgery reducing the likelihood that a piece may be inadvertently left in a patient. Yet the head frame apparatus and devices enable flexibility in positioning the endotracheal tube and anesthesia delivery circuit to reduce the risk of injury caused by a restricted flow of oxygen as well as enable ease of use which reduces the amount of time in surgery and may lead to more successful surgical results.

In an embodiment, the first arched member of the head frame apparatus is in the form of a curved rectangular member having a first, second, third and fourth side. The second arched member of the head frame apparatus is in the form of a curved rectangular member having a first, second, third and fourth side. The first arched member has a plurality of threaded openings from the first side to the third side. The third side of the first arched member is positioned next to the human head. The plurality of threaded openings in the first arched member receive a plurality of screws to be inserted into the human head. The second arched member also has a plurality of threaded openings from the first side to the third side. The third side of the second arched member is positioned next to the human head and the plurality of threaded openings receive a plurality of screws to be inserted into the human head.

In an embodiment, the removable rectangular device is coupled to the second arched member and includes a bottom, a first side and a second side to position the endotracheal tube. The first side has a threaded opening to receive a screw having a flat surface at the end of the screw to secure the endotracheal tube against the second side.

In an embodiment, two other removable devices are coupled to the first arched member and each include openings to position the anesthesia delivery circuit and slotted openings to be inserted onto at least a portion of the first, second and fourth sides of the first arched member. The two other removable devices each include threaded openings to receive set screws to position each removable device to the first arched member.

In an embodiment, the mount of the head frame apparatus is a parallel rail connector mount having a lever for the securing and releasing of the removable reference indicator. Other types of mounts may be difficult to manufacture as well as operate.

In an embodiment, the removable reference indicator includes a universal joint having first and second ends. The first end of the universal joint is coupled to a base and a plate is coupled to the second end of the universal joint. A block having a first hole and a second hole is coupled to the plate. A pointer with an attached ruler is inserted into the first hole and a set screw is inserted into the second hole to secure the pointer in order to indicate a reference point.

The use of a universal joint allows for setting a reference point by adjusting a single lever. Other reference indicators may be difficult to manufacture as well as operate. Other reference indicators may have multiple levers to operate as opposed to the single lever of the universal joint. Additional time in surgery may be required in using reference indicators with multiple levers.

In an embodiment, the base of the removable reference indicator includes a first and second rail that are parallel to each other and each rail has a cross section having the shape of a diamond. Further, the plate of the removable reference indicator includes a slot to be secured by a first screw at the second end of the universal joint and the plate is secured to a first side of the block by at least a second screw. In an embodiment, the pointer has a first end having a diameter greater than a diameter of the first hole in the first block and the pointer has a second end to indicate the reference point.

The removable reference indicator may be transported by a transport apparatus having parallel rail connector mounts to secure and easily remove the removable reference indicator before or during surgery. The transport apparatus also includes removable handles that protect the position of the removable reference indicator from being inadvertently moved as well as provide handles in transportation.

In an embodiment, the transport apparatus includes a base having a first and second end. A parallel rail connector mount is coupled to the base between the first and second ends. The parallel rail connector mount secures the removable reference indicator that identifiers the reference point in relation to a human head during surgery. The transport apparatus also includes a first removable handle coupled to the first end and a second removable handle coupled to the second end. The parallel rail connector mount includes a lever to attach and release the removable reference indicator quickly.

In an embodiment, the transport base includes a first and second post to insert a first and second cylinder of the first removable handle. The transport base also includes a third and fourth post to insert a third and fourth cylinder of the second removable handle. The first, second, third and fourth cylinders have a hole to insert a first, second, third and fourth set screw to secure the first and second removable handles to the first, second, third and fourth posts.

In an embodiment, the transport base is in the form of a rectangle and the first, second, third and fourth posts are positioned at the corners of the rectangular base. The first and second cylinders are coupled by a first horizontal handpiece member and the third and fourth cylinders are coupled by a second horizontal handpiece member.

In an embodiment, an apparatus provides reference points in relation to casts of teeth/jaw used in an articulator during preoperative modeling. The apparatus includes a plate having a first side to secure a cast used in an articulator and a second side having a plurality of rectangular slots. A rectangular member is inserted into one of the plurality of rectangular slots. The rectangular member that extends beyond an edge of the plate includes a square opening to insert a bendable reference indicator having a pointer at the end. The bendable reference indicator has a first square end which is inserted into the square opening and a thin pointer end that is bendable to provide the reference point in relation to the cast.

In an embodiment, the apparatus includes a disk inserted into one of the plurality of slots. A rectangular member is coupled to the disk and extends beyond an edge of the plate. Similar to the above, the rectangular member extends beyond an edge of the plate and includes a square opening to insert a bendable reference indicator. The bendable reference indicator has a first square end which is inserted into the square opening and a thin pointer end that is bendable to provide the reference point in relation to the cast. The use of the disk and rectangular member are typically easier to manufacture than other embodiments.

In an embodiment, an orbiting segment apparatus positions a portion of a cast of a jaw in an articulator. The orbiting segment apparatus include a base having at least one opening to position at least one rod to be attached to a portion of the cast. A first member has a first end attached to the base and a second end. A second member has a first end forming a socket to be coupled to a condyle ball of the articulator. The second member has an interface at the second end to be coupled to the second end of the first member. A set device and screw, such as a clamp, allows the first member to extend in relation to the second member when the set device is released and the set device fixes the first member in relation to the second member with the set device is secured.

FIG. 1 illustrates a head frame apparatus 100 to position an endotracheal (breathing) tube 101, an anesthesia delivery circuit and removable reference indicator 102 used in maxillofacial surgery according to an embodiment. Head frame apparatus 100 is typically positioned on a patient's head 103 during surgery as illustrated in FIG. 1. Head frame apparatus 100 includes an arched member 100a coupled to another arched member 100b. In an embodiment, arched members 100a and 100b are in the form of curved rectangular members having four sides with one side facing the patient's head 103. In an embodiment, arched member 100a is positioned on the top of the patient's head 103 and arched member 100b is positioned approximately 90 degrees so that arched member 100b surrounds the patient's face.

In an embodiment, screws 104a-h are inserted into threaded holes 105a-h to secure head frame apparatus 100 to the patient's head 103. In an embodiment, set washers 106a-h are used to limit the depth of insertion. In alternate embodiments, fewer or more screws may be used. In alternate embodiments, other types of screws may be used. In alternate embodiments, other securing mechanisms other than screws may be used.

FIGS. 1 and 2A-C illustrate removable devices 107a-b and 108 that may be coupled to head frame apparatus 100 and are used to position an endotracheal tube 101 and an anesthesia delivery circuit (including input tube 133a, output tube 133b and y-connector 133c that is attached to endotracheal tube 101). Rather than using removable devices 107a-b and 108, surgery would often be performed with just taping or wrapping an endotracheal tube 101 and an anesthesia delivery circuit to patient's head 103. However, a taped or wrapped endotracheal tube 101 or anesthesia delivery circuit may become restricted during surgery and lead to an adverse condition of the patient, such as cardiac arrest. Removable devices 107a-b and 108 enable the endotracheal tube 101 or anesthesia delivery circuit to be secured to head frame apparatus 100, while reducing the risk that the endotracheal tube 101 or anesthesia delivery circuit could be constricted. Removable device 107a-b may be placed in any position on arched member 100a such that an anesthesia delivery circuit does not overly interfere with surgery operations, but still does not restrict the flow of oxygen. Removable devices 107a-b may even be repositioned on arched member 100a during surgery to accommodate the surgeon's access to the face during different phases of the surgery while not increasing the risk of restricting oxygen flow.

Each of the removable devices 107a-b includes a rectangular slotted opening 109 to be inserted onto arched member 100a at the desired position. In an embodiment, a screw 111 is inserted into thread opening 112 so that the slotted opening 109 is secured to at least three sides of arched member 100a. Each of the removable devices 107a-b also has a curved u-shaped opening 110 for positioning a input tube 133a and a output tube 133b while not restricting the flow of oxygen. In alternate embodiments, more removable devices 107 may be coupled to arched member 100a and used for other tubes. In an embodiment, input tube 133a carries oxygen and anesthesia gas or agents from an oxygen/anesthesia source to y-connector 133c and ultimately to the patient by way of endotracheal tube 101, while output tube 133b exhausts carbon dioxide from the patient by way of y-connector 133c and endotracheal tube 101.

Removable device 108 is also coupled to arched member 100b to position and secure endotracheal tube 101. In an embodiment, removable device 108 includes a rectangular trough 115 having three sides with a threaded opening 113 on one side to insert a set screw 114 to secure endotracheal tube 101. Rectangular trough 115 also includes a tongue or extension 121 for positioning the endotracheal tube 101. Set screw 114 may be turned enough to secure the endotracheal tube 101, but not restrict the flow of oxygen. Also, one side of rectangular trough 115 includes a lip to secure endotracheal tube 101. Removable member 108 also includes a post 120 extending from a side of rectangular trough 115. Removable member 108 is coupled to arched member 100b, and similarly adjustable, by inserting post 120 into clamp 116. After the appropriate angle for the rectangular trough 115 is determined in relation to the arched member 100b, screw 117 may be tightened by way of threaded opening 118 on arched member 100b to secure the angle, or the position of extension 121 (and thus the endotracheal tube 101) in relation to arched member 100b.

Figure 3:
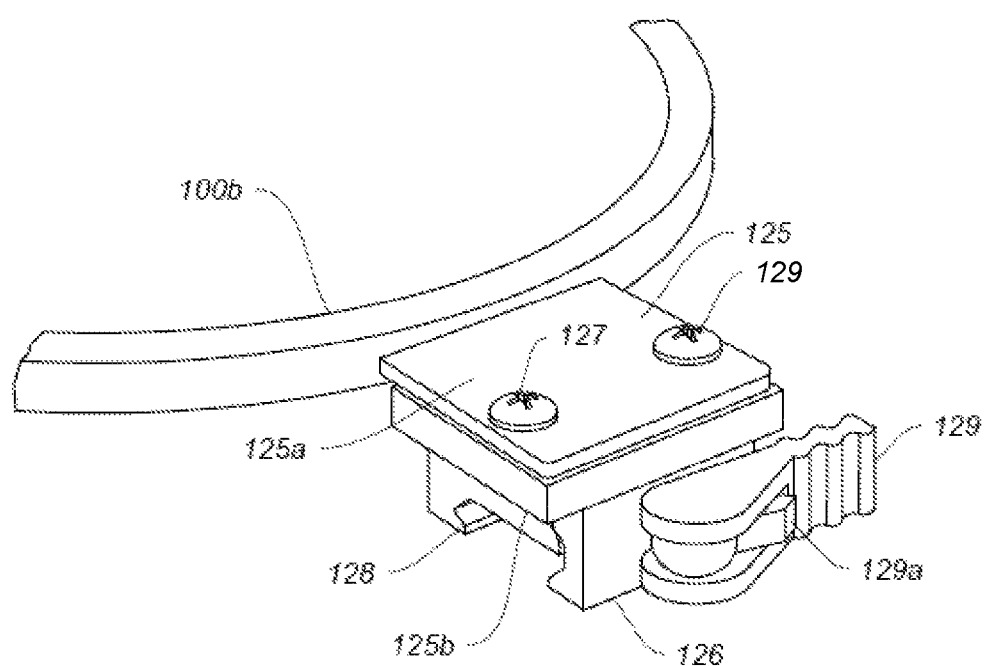
FIG. 3 illustrates a device coupled to the head frame apparatus to position a removable reference indicator according to an embodiment.

FIG. 3 illustrates a plate 125 coupled to arched member 100b to provide a mount 126 for removable reference indicator 102. In an embodiment, plate 125 is a rectangular plate having a top side 125a and bottom side 125b. A side of plate 125 is soldered to an outer side of arched member 100b in an embodiment. Mount 126 is coupled to the bottom side 125a by way of screws 127 and 129. In an embodiment, mount 126 is a parallel rail connector mount having a lever 129 to release and attach removable reference indicator 102. In an embodiment, lever 129 is known as a quick release lever. In an embodiment, lever 129 is positioned away from the patient's face so as to allow for easy insertion and release of the removable reference indicator 102 to and from mount 126. In an embodiment, mount 126 is a Picatinny mount or rail. In an embodiment, button 129a is pushed and lever 129 is pulled away from arched member 100b. A removable reference indicator 102 then may be placed in the mount and secured by rotating the lever 129 towards arched member 100b.

Figure 4:
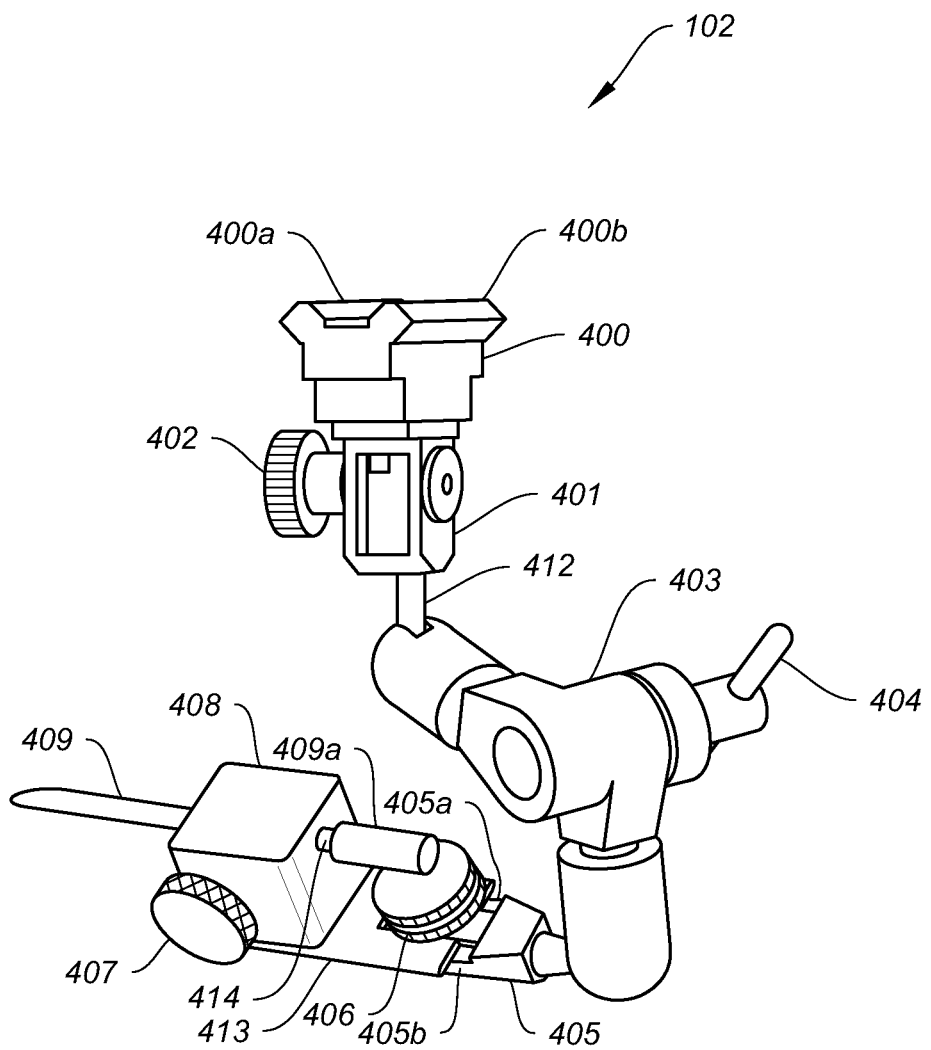
FIG. 4 illustrates a removable reference indicator according to an embodiment.

FIG. 4 illustrates a removable reference indicator 102 that may be removed from or secured to head frame 100 according to an embodiment. In an embodiment, removable reference indicator 102 includes universal joint 403 that is positioned by tightening or turning lever 404 clockwise. Similarly, universal joint 403 is released by turning lever 404 counter clockwise. By at least adjusting universal joint 403, a reference point for a portion of the face may be adjusted by way of positioning reference pointer 409 at the end of removable reference indicator 102.

In particular, removable reference indicator 102 includes a base 400 having parallel rails 400a-b that are inserted into rail grooves 128 of mount 126 shown in FIG. 3 in order to position removable reference indicator 102 relative to the patient's face. As described above, pushing lever 129 away from arched member 100b, after pushing release button 129a, allows for the insertion of parallel rails 400a-b into rail grooves 128 of mount 126. Pushing lever 129 toward arched member 100b secures removable reference indicator 102 to mount 126. Rotating screw 402 counter clockwise allows for the removal of base 400 from block 401. Rotating screw 402 clockwise allows for tightening or securing of block 400 to block 401. Member 412 extends from block 401 and includes a ball (not shown) which is coupled to a first end of universal joint 403 that includes a first socket to position the ball of member 412. A second end of universal joint 403 includes a second socket that is coupled to a ball (not shown) of an interface 405 having recessed inserts 405a-b.

A forked plate 413 is inserted into recessed inserts 405a-b of interface 405 and secured by rotating set screw 406 clockwise. Forked plate 412 is released by rotating set screw 406 counter clockwise. Block 408 is secured to forked plate 413 by screws (not shown). Reference pointer 409 is inserted into block 408, in particular hole 414, and secured by rotating set screw 407 clockwise. Similarly, reference pointer 409 is released by rotating set screw 407 counter clockwise. Cylindrical base 409a limits reference pointer 409 from extending beyond the cylindrical base 409a and block 408 interface.

FIGS. 10A-C illustrate an alternate reference pointer that may be used in the removable reference indicator 102 according to an embodiment. In particular, FIGS. 10A-C illustrate a reference pointer 1000 that may be used instead of pointer 409 illustrated in FIG. 4. Pointer 1000 includes a first rod portion 1000a and second sleeve portion 1000b. In an embodiment, second portion 1000b has a ruler 1000c attached to aid in measurements. Portion 1000a includes a cylindrical base coupled to rod 1000d. Sleeve portion 1000b includes a hollow cylinder having a first exterior diameter portion 1000e, a second exterior diameter portion and a third exterior diameter portion 1000d. Rod 1000d is inserted into a hole at first exterior diameter portion 1000e. Reference pointer 1000 is operated similar to reference pointer 409. Reference pointer 1000 may be inserted into hole 414 of block 406 with the end or tip of rod 1000d identifying a reference point on a patient face. However, first rod portion 1000a may be extracted by a predetermined distance (or measurement) indicated by ruler 1000c in order to aid the surgeon in knowing where to reposition a portion of the face in relation to the fixed reference point that is identified when first rod portion 1000a is inserted completely into sleeve portion 1000b.

Figure 5A:
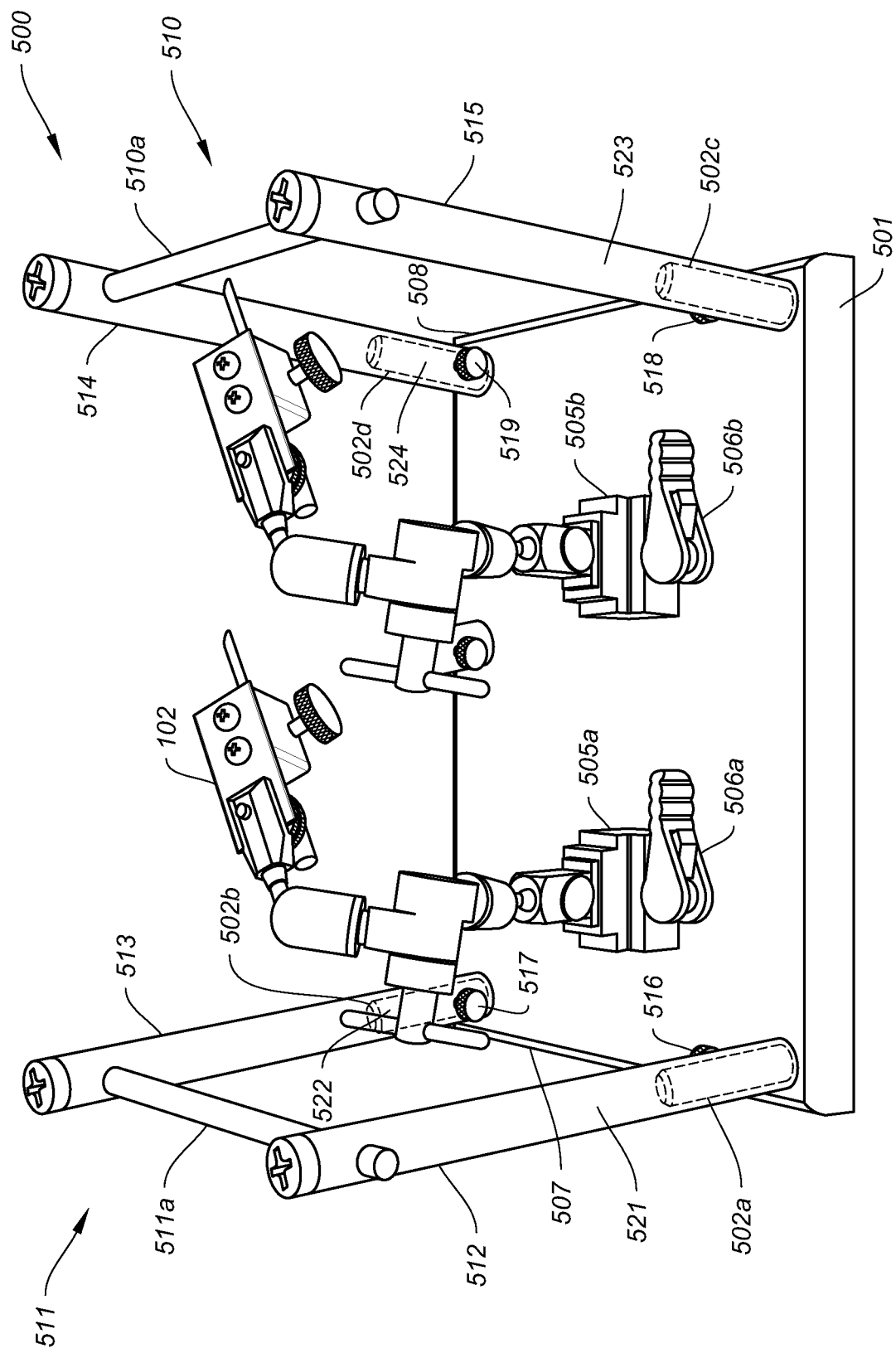
FIGS. 5A-B illustrate a transporting apparatus to transport and position a removable reference indicator according to an embodiment.
Figure 5B:
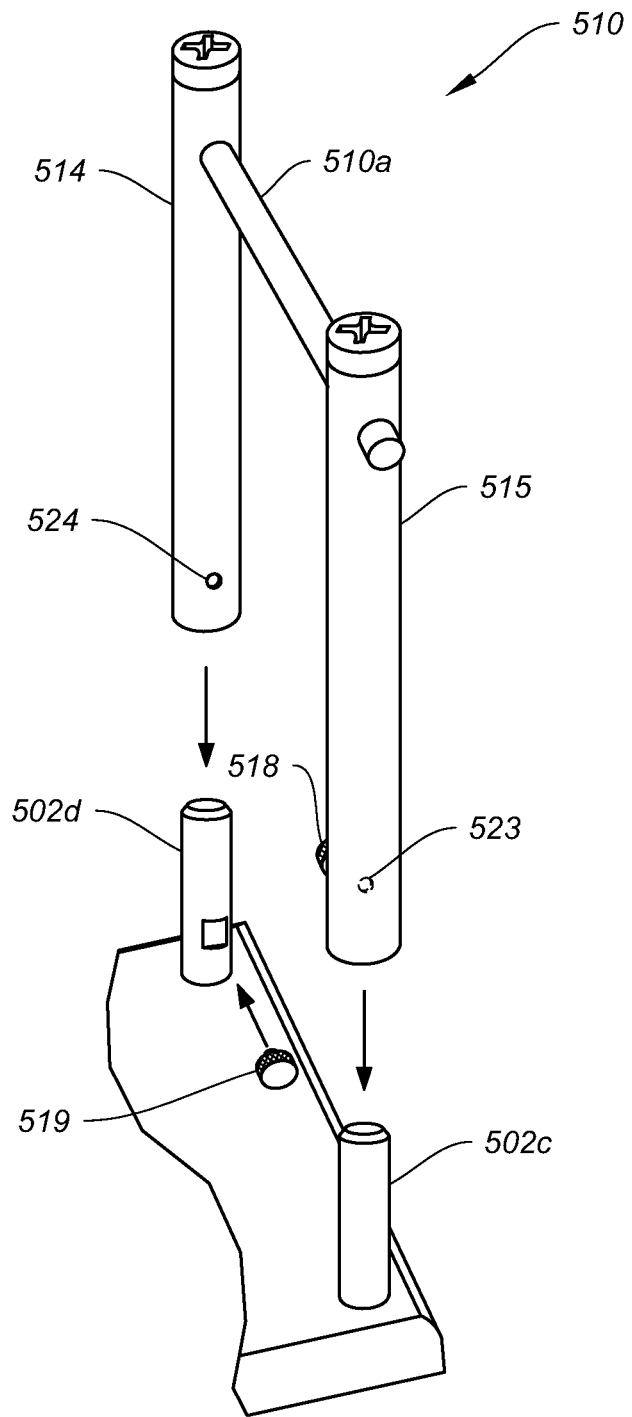

FIGS. 5A-B illustrate a transporting apparatus 500 to transport removable reference indicator 102 according to an embodiment. Transport apparatus 500 is used to both transport and protect removable reference indicator 102 from inadvertently being moved or adjusted before or after being positioned on head frame apparatus 100. Often reference indicators are calibrated or set before surgery; however, during surgery, or shortly before, operation personnel, such as a surgical nurse, may inadvertently adjust the removable reference indicators during transportation to the surgeon. Also after mounting removable reference indicator 102 onto head frame apparatus 100 and setting pointer 409 to the correct reference point on the patient's face, the removable reference indicator 102 may be removed and stored in transport apparatus 500 while the surgeon makes necessary cuts and then remounted in order to once again have a fixed reference point. Transport apparatus 500 also has mounts 505a-b for easily securing and accessing removable reference indicators that have been pre-aligned. In an embodiment, mounts 505a-b are similar to and operate similar to mount 126 shown in FIG. 3.

Transport apparatus 500 includes a rectangular base 501 having four posts 502a-d at respective corners. While transport apparatus 500 includes a rectangular base in an embodiment, other geometrical shapes may be used in other embodiments. In an embodiment, rectangular base 501 is made of aluminum or polymer such as delrin. In an embodiment, rectangular base 501 has two mounts 505a-b for securing removable reference indicators, such as removable reference indicator 102. In embodiments, mounts 505a-b are parallel rail mounts with a quick release leaver 506a-b, respectively. In an embodiment, mounts 505a-b are Picatinny mounts. Mounts 505a-b are positioned between ends 507 and 508 of rectangular base 501.

In an embodiment, transport apparatus 500 has removable handles 510 and 511 which include handpieces 510a and 511a as well as hollow cylinders 512-515. The removable handles 510 are 511 are used to protect the removable reference indicators from being unintentionally altered before being mounted as well as allow a mechanism to hold and transport the removable reference indicators. When the removable reference indicators are to be used, the handles 510 and 511 may be easily removed without altering the preset removable reference indicators.

In an embodiment, hollow cylinders 512-515 are inserted over posts 502a-d. Each hollow cylinder 512-515 has threaded opening 521-524 to have set screws 516-519 secure the hollow cylinders 512-515 to posts 502a-d by rotating the set screws 516-519 clockwise. Similarly, removable handles 510 and 511 are removed by rotating set screws 516-519 counter clockwise and lifting hollow cylinders 512-515 from posts 502a-d.

Figure 9A:
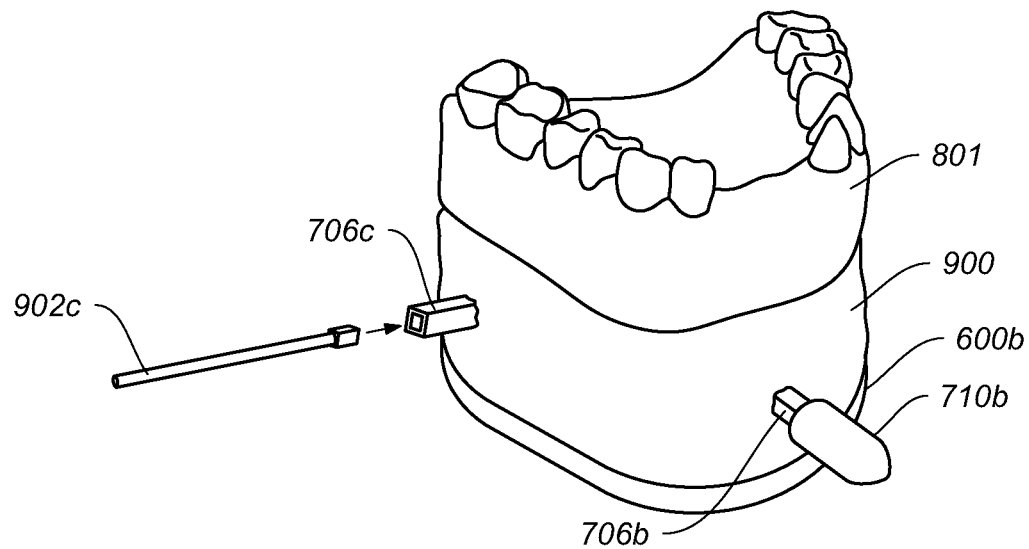
Figure 9B:
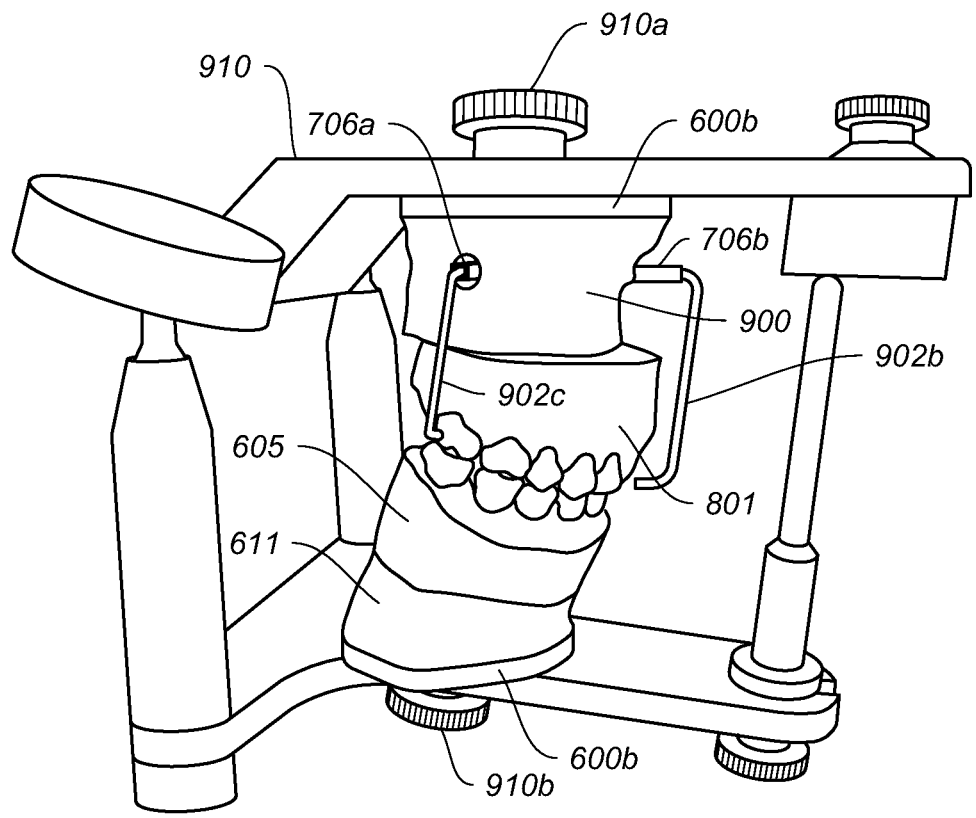

FIGS. 6A, 6B and 6D illustrate an apparatus or system to identify reference points of a cast in an articulator used in preoperative maxillofacial surgery modeling according to an embodiment. In particular, FIGS. 6A and 6D illustrate first and second sides of a plate 600a, to position a cast, such as a cast of the maxillary (upper) teeth 605 as seen in FIGS. 6B and 9B. In an embodiment, plate 600a is a one-time-use plate that is provided with the articular 910 as described below. Plate 600a has a thread opening 610 on a first side to be coupled to an articulator by a screw, such as screw 910b of articulator 910 shown in FIG. 9B. The second side of plate 600a includes a plurality of rectangular slots formed between pairs of rectangular ridges 604a-d with a portion of the rectangular members 601a-b extending beyond an edge of plate 600a. In an embodiment, rectangular members 601*a-b* are glued to the second side of plate 600. After rectangular members 601*a-b* are positioned, cast 605 is coupled to the second side of plate 600*a* by plaster 611. In an alternate embodiment, plate 600*a* does not include a plurality of ridges 604*a-d* on the second side.

At the end of each of the rectangular members 601*a-b*, rectangular openings 602*a-b* are formed to receive bendable reference indicators, such as bendable reference indicator 603 shown in FIG. 6B (and bendable reference indicator 603 before bending or straight as shown in FIG. 6C). Bendable reference indicator 603 is illustrated as bent showing an important reference point for cast 605 at the point of bendable reference indicator 603 in FIG. 6B. In embodiments, reference points may be particular teeth in the cast (or on the patient), such maxillary incisors, right first molar, and/or left first molar. Rectangular openings 602*a-b* are oriented in relation to cast 605 such that it is more easy to bend an inserted bendable reference indicator. In an embodiment, a corner of rectangular openings 602*a-b* is positioned toward cast 605. In an embodiment, rectangular openings 602*a-b* are formed by cutting portions of hollow rectangular brass rods and fixing them to rectangular members 601*a-b*. In an embodiment, a bendable reference indicator has a stronger and thicker rectangular portion 603*a*, as shown in FIG. 3C, to be inserted into rectangular openings 602*a-b*, while having a more lighter and thinner cylindrical pointer portion towards the end closest the cast in order to enable easy bending and thus easier identification of modeling reference points. In embodiments, bendable reference indicators are made of a malleable metal.

Bendable reference indicator systems as illustrated in FIGS. 6A, 6B, 6D and 7A-B typically provide benefits over other modeling techniques. Bendable reference indicators and there indicated reference points are kept with the model (or cast) for later study. This is possible because the bendable reference indicator mounts and bendable reference indicators (or pointers) are attached to the cast and one-time-use plate 600*a-b* in an embodiment. Some modeling techniques measure from an articulator so that when the models/casts are removed from the articulator, the indicated reference point is lost. After modeling, a surgeon will then be able to know the approximate distances to reposition certain portions of the face. For example, the modeling would tell the surgeon that a patient's lower jaw would need to be moved three fourths of an inch out in relation to a fixed reference point of the upper jaw, such as the right maxillary incisor.

Figure 7A:
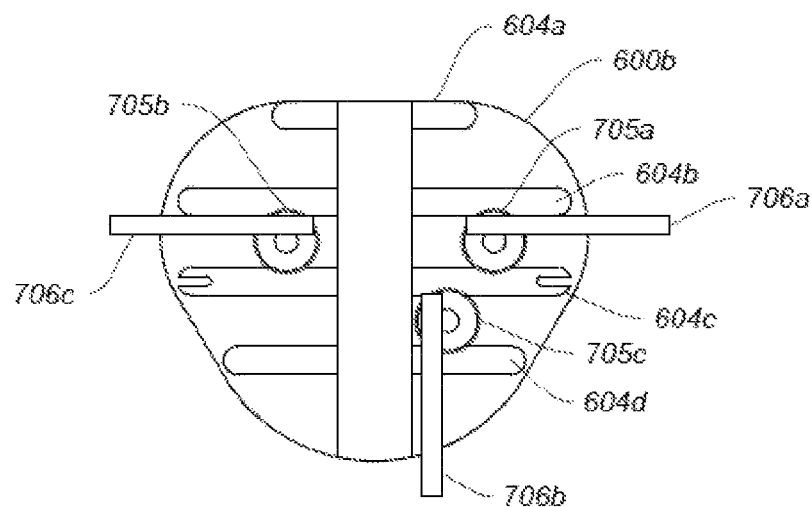
FIGS. 7A-B illustrate a system to identify reference points of a cast in an articulator used in preoperative modeling according to an embodiment.
Figure 7B:
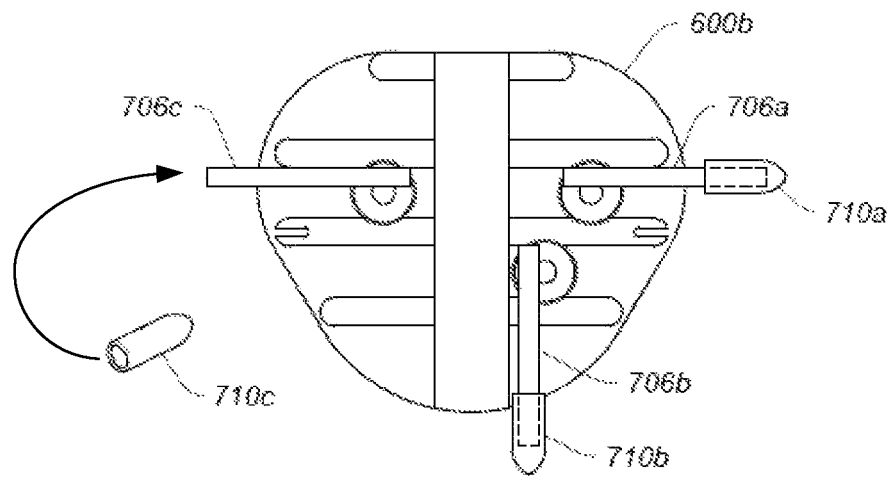

FIGS. 7A-B illustrate an alternate apparatus or system to identify reference points of a cast for an articulator 910 used in preoperative maxillofacial surgery modeling according to embodiments. In particular, FIGS. 7A-B illustrate an apparatus that may be more easily manufactured. Rather than using rectangular members 601*a-b*, brass disks 705*a-c* may be glued or otherwise inserted between rectangular ridges 604*a-d*. In an embodiment, set screws are housed in each brass disk 705*a-c*. When the set screw is turned clockwise, a screw end extends toward plate 600*b* causing a brass disk 705*a-c* to be wedged into place against pairs of rectangular ridges 604*a-d*. Hollow rectangular brass rods 706*a-c* then may be soldered to brass disks 705*a-c*. Plastics caps 710*a-c* may be used to cover the openings of hollow rectangular brass rods 706*a-c* when plaster 900 is applied to secure a cast to plate 600*b* as illustrated in FIG. 9A. Bendable reference indicators 902*b-c* may then be inserted into hollow rectangular brass rods 706*a-b* as similarly described above in regards to FIGS. 6A-D and illustrated in FIGS. 9A-B.

Figure 8:
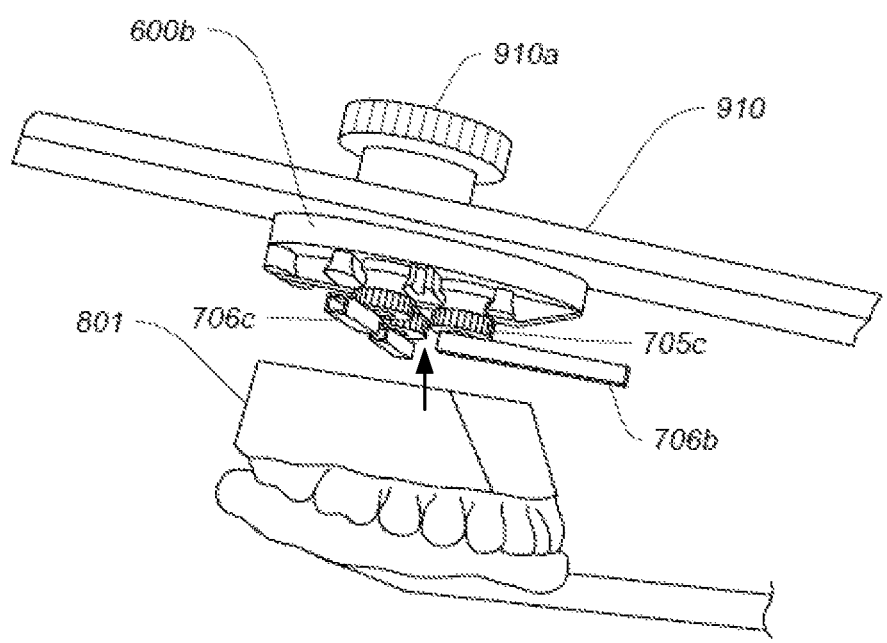
FIGS. 8 and 9A-B illustrates a system shown in FIGS. 7A-B in relation to an articulator and cast according to an embodiment.

FIGS. 8 and 9A-B illustrate a bendable reference indicator system shown in FIGS. 7A-B in relation to an articulator 910 and cast according to an embodiment. In particular, FIG. 8 illustrates a cast of the maxilla (upper jaw) 801 that is to be coupled to plate 600*b* having rectangular hollow rods 706*b-c* and disks, such as disk 705*c*, before plaster 900 is applied as illustrated in FIG. 9A. The plate 600*b* is coupled to articulator 910 by screw 910*a* as illustrated in FIGS. 8 and 9B.

Diagnosis and surgical planning involves use of articulators, such as dental articulators, with a patient derived plaster cast or models of their teeth. In some configurations of jaw reconstruction, a segment of the jaw and teeth are moved to a more desirable location. If the jaw segment is continuous with the jaw joint (temporomandibular joint), then the degree of freedom of movement is restricted by the position of the jaw joint. The segment of the jaw can be moved but its movement rotates about the jaw joint. To be simulated on the dental articulator, an orbiting segment apparatus is used to maintain the rotating relationship of the mobilized plaster segment to a condyle ball on the articulator. The condyle ball represents the anatomical jaw joint of the patient. In an embodiment, an orbiting segment apparatus is a type of mechanical jig.

Figure 11A:
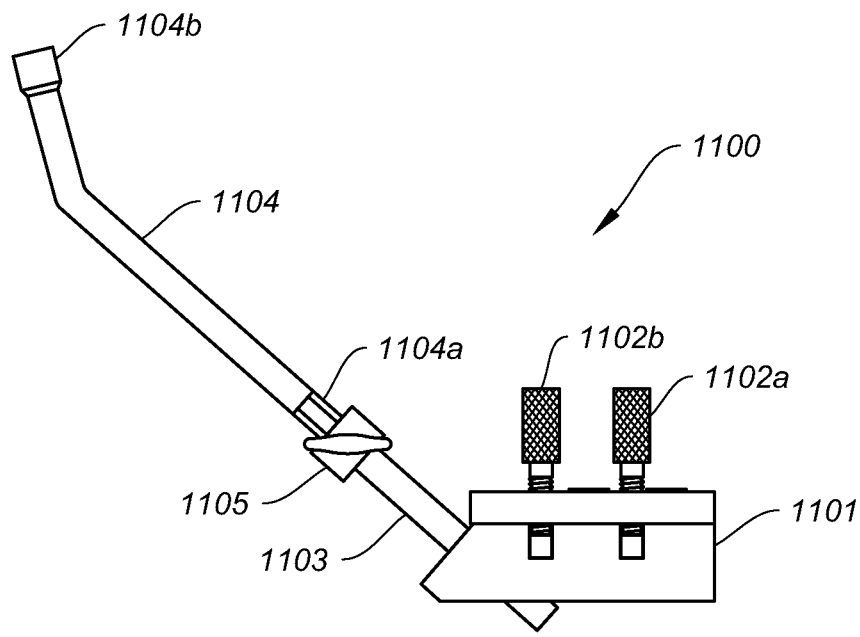
FIGS. 11A-B illustrate an orbiting segment apparatus that may be used in an articulator according to an embodiment.
Figure 11B:
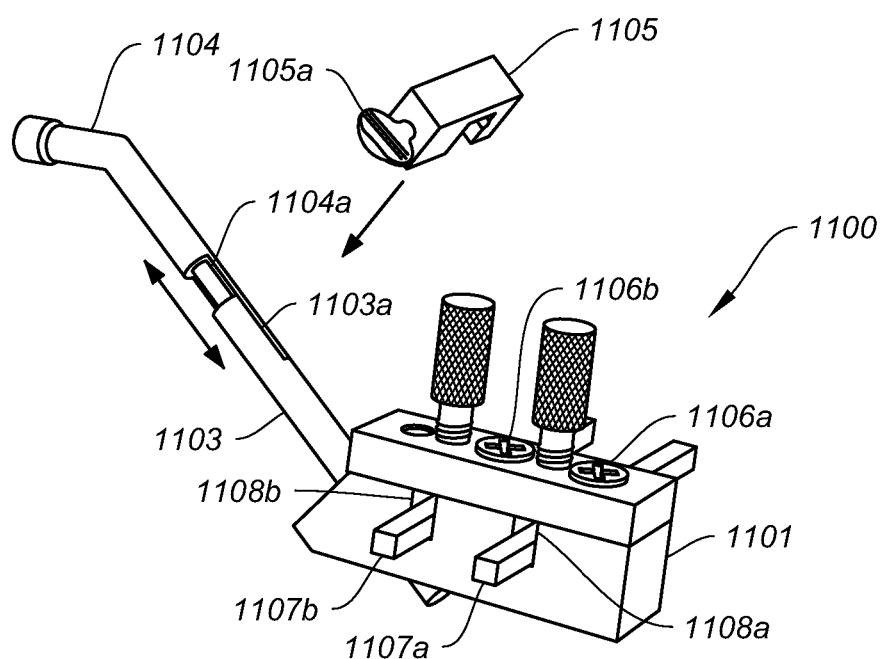
Figure 12:
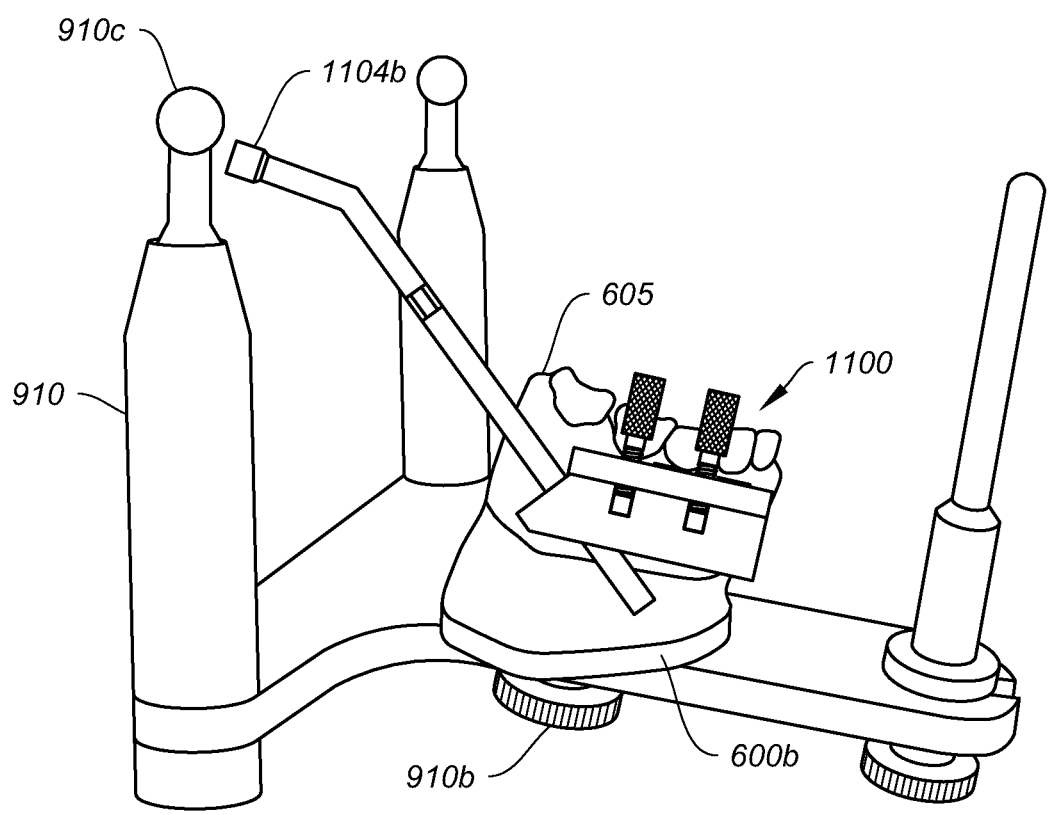
FIGS. 12 and 13 illustrate an orbiting segment apparatus that positions a portion of a cast in an articulator according to an embodiment.

FIGS. 11A-B illustrate an orbiting segment apparatus 1100 that may be used in an articulator 910 according to an embodiment. Orbiting segment apparatus 1100 includes a base 1101 having openings 1108*a-b* for rectangular pins or rods 1107*a-b*. Set screws 1102*a-b* release and secure the rectangular rods 1107*a-b* in openings 1108*a-b*. In an embodiment, base 1101 includes a top portion and a bottom portion secured by screws 1106*a-b*. A cylindrical member 1103 is coupled to base 1101 and includes an interface 1103*a* to be mated with interface 1104*a* of cylindrical member 1104. Interface 1104*a* includes a male semi-circle portion that is mated with a female semi-circle portion 1103*a*. The interfaces 1103*a* and 1104*a* allow for cylindrical members 1104 to extend from cylindrical member 1103 while a socket interface 1104*b* may be in contact with condyle ball 910*c* of articular 910 as shown in FIG. 12. Set device 1105 and screw 1105*a* are used to secure and release the relative position of cylindrical member 1104 in relation to cylindrical member 1103. Turning screw 1105*a* clockwise secures the relative position of cylindrical member 1104 in relation to cylindrical member 1103, while turning screw 1105*a* counter clockwise releases the coupling of cylindrical member 1104 in relation to cylindrical member 1103. In an embodiment, set device 1105 and screw 1105*a* is a clamp.

Figure 13:
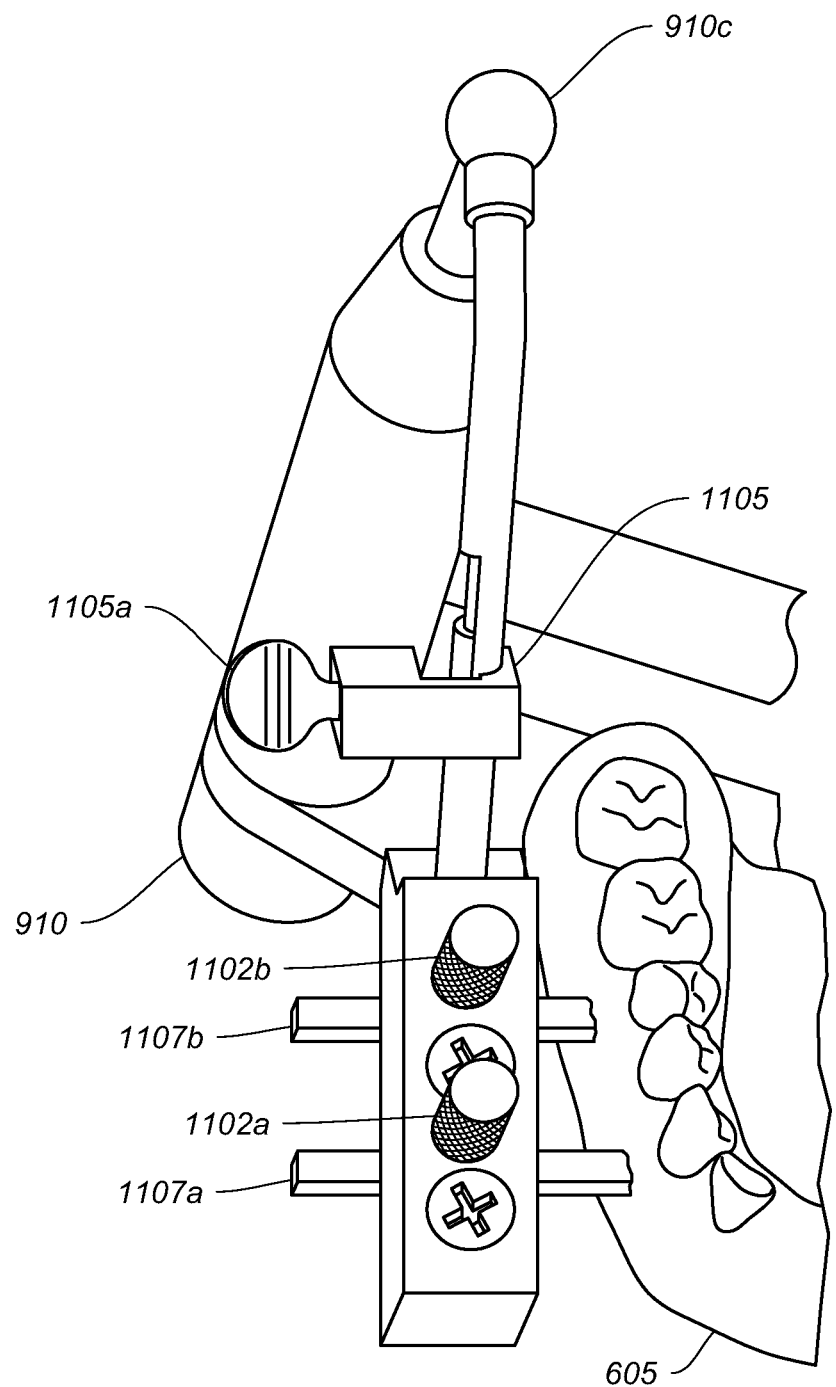

FIGS. 12 and 13 illustrate orbiting segment apparatus 1100 that positions a portion of a cast 605 in an articulator 910 according to an embodiment. Ends of rectangular rods 1107*a-b* are imbedded into the cast model 605 and cemented with acrylic resin in an embodiment. Base 1101 having openings 1108*a-b* is engaged with rectangular rods 1107*a-b*. The acrylic is allowed to set with socket interface 1104*b* touching condyle ball 910*c* when cylindrical members 1104 and 1105 are extended and set device 1105 and screw 1105*a* secure the cylindrical members 1104 and 1105 relative position.

A portion of the cast model 605 may be cut and moved to model a possible cut during surgery. After determining an ideal positioning of a portion of the cast 605 in preoperative modeling, socket interface 1104*b* still should be contacting condyle ball 910*c* of articulator 910. In order to remove cast 605 from articulator 910 for further study, set device 1105 and screw 1104*a* is removed in order to collapse or disengage cylindrical member 1104 from cylindrical member 1103. Without being able to disengage the cylindrical members 1104 and 1103, the cast 605 cannot be removed from the articulator 910 because orbiting segment apparatus 1100 traps the cast 605 in place.

A critical objective of maxillofacial surgery is to correctly reposition the teeth. Correct repositioning of the teeth is important in achieving a functional and cosmetically beneficial result. During both model surgery and patient surgery, portions of the plaster jaw or patient jaw are completely mobilized. The original position of the mobilized position is lost. To correctly reposition the mobilized portion (either the plaster portion or the actual patient portion) some reference point must remain immobilized. The removable reference indicator with the head frame as well as the bendable reference indicator system and orbiting segment apparatus maintain a reference point in space that is the original position. By comparing the original position or reference point after repositioning, the net change can be known. Without the maintenance of some original reference point or landmark, there is no way to know if correct repositioning has occurred.

Although illustrative embodiments are shown and described herein, many variations and modifications are possible which remain within the concept, scope, and spirit of the claims, and these variations would become clear to those of ordinary skill in the art after perusal of this application. Accordingly, the present embodiments are to be considered as illustrative and not restrictive, and the invention is not to be limited to the details given herein, but may be modified within the scope and equivalents of the appended claims.

I claim:

1. An apparatus to provide a reference point in relation to a human head during surgery, the apparatus attachable to a human head frame to be positioned on and supported by the human head during surgery, comprising:
   a base having a first and second rail each having a length and constructed to be slidably received in a direction along their length in a mount of the head frame;
   a universal joint having first and second ends, the first end coupled to the base;
   a plate coupled to the second end of the universal joint;
   a block having a first hole and a second hole, the block coupled to the plate;
   a pointer to be inserted into the first hole; and
   a set screw to be inserted into the second hole to secure the pointer in order to indicate the reference point.

2. The apparatus of claim 1,
   wherein the first and second rails are parallel to each other and configured to mate to first and second parallel grooves of the mount.

3. The apparatus of claim 1,
   wherein each rail has a cross section having substantially the shape of a diamond.

4. The apparatus of claim 1,
   wherein the plate includes a slot to be secured by a first screw at the second end of the universal joint.

5. The apparatus of claim 4,
   wherein the plate is secured to a first side of the block by at least a second screw.

6. The apparatus of claim 1,
   wherein the pointer has a first end having a diameter greater than a diameter of the first hole in the block, and
   wherein the pointer has a second end to indicate the reference point.

7. The apparatus of claim 1, wherein the pointer includes a rod inserted into a hollow sleeve, and wherein the hollow sleeve includes a ruler to measure a distance from the reference point that is identified by the end of the rod.

8. The apparatus of claim 1,
   further including a securing lever on the mount which is movable between a first position to allow movement of the base relative to the mount and a second position preventing movement of the base relative to the mount.

\* \* \* \* \*